United States Patent [19]

Degen et al.

[11] Patent Number: 4,960,523

[45] Date of Patent: Oct. 2, 1990

[54] PROCESS FOR WORKING UP HYDROLYSIS RESIDUES FROM THE SYNTHESIS OF ORGANOCHLOROSILANES

[75] Inventors: Bruno Degen, Much; Kurt Feldner, Leverkusen, both of Fed. Rep. of Germany

[73] Assignee: Bayer Aktiengesellschaft, Leverkusen, Fed. Rep. of Germany

[21] Appl. No.: 394,608

[22] Filed: Aug. 16, 1989

[30] Foreign Application Priority Data

Sep. 1, 1988 [DE] Fed. Rep. of Germany ....... 3829582

[51] Int. Cl.⁵ ............................................. C02F 1/72
[52] U.S. Cl. ................................. 210/721; 210/758; 210/728; 210/729; 556/477
[58] Field of Search ............... 210/708, 710, 717, 721, 210/758, 728, 729; 252/321, 351, 354; 556/472, 477

[56] References Cited

U.S. PATENT DOCUMENTS

| | | | |
|---|---|---|---|
| 2,380,995 | 8/1945 | Rochow | 556/472 |
| 4,221,691 | 9/1980 | Danielson et al. | 260/33.6 SB |
| 4,244,818 | 1/1981 | Abson | 210/721 |
| 4,408,030 | 10/1983 | Marko | 528/10 |
| 4,568,475 | 2/1986 | Roe et al. | 210/778 |
| 4,758,352 | 7/1988 | Feldner | 210/719 |

FOREIGN PATENT DOCUMENTS

| | | |
|---|---|---|
| 0210418 | 2/1987 | European Pat. Off. |
| 2362494 | 7/1975 | Fed. Rep. of Germany |
| 2079698 | 10/1971 | France ............... 210/778 |

Primary Examiner—Peter Hruskoci
Assistant Examiner—Krisanne Shideler
Attorney, Agent, or Firm—Sprung Horn Kramer & Woods

[57] ABSTRACT

A process is disclosed for working up the high-boiling, solids-containing residues obtained in the synthesis of organochlorosilanes which are hydrolyzed and then optionally oxidized, comprising adding during hydrolysis and/or oxidation a surface-active agent which hydrophilicizes the surface of the solids.

6 Claims, 1 Drawing Sheet

PROCESS FOR WORKING UP HYDROLYSIS RESIDUES FROM THE SYNTHESIS OF ORGANOCHLOROSILANES

BACKGROUND OF THE INVENTION

1. Field of the Invention

This invention relates to a process for working up hydrolysis residues obtained in the hydrolysis of solids-containing polysilane sludges from the synthesis of organochlorosilanes by the direct process. More particularly, the invention relates to the working up of hydrolysis reisdues from the synthesis of methylchlorosilanes.

2. Background Information

Organochlorosilanes and, in particular, methylchlorosilanes are used as starting materials for the production of silicones which are widely used, for example, as rubbers, jointing compounds, oils, structural sealants, etc. Dimethyldichlorosilane is required in particular for the production of methylchlorosilanes, being obtained in high yields when the direct reaction of silicon with methyl chloride is catalyzed by copper or copper compounds. The process is described in principle in U.S. Pat. No. 2,380,995. The industrial production of methylchlorosilanes by this process is carried out worldwide, the reaction normally being carried out in continuous fluidized-bed reactors.

Where the direct process is carried out in fluidized-bed reactors, the very fine fractions of silicon, catalyst and unreacted contact material are continuously discharged together with the reaction products, the crude silane mixture, and unreacted methyl chloride.

These dust-like fines are often collected together with the highest-boiling reaction products ($Bp_{760} > 160°$ C.) in a so-called sludge vessel followed by a washing tower. The temperature of the vessle, which is under the usual excess pressure of 1.5–10 bar, is generally adjusted so that the mixture of solids and condensed fractions is kept sufficiently thinly liquid to facilitate discharge from the vessel.

According to DE-PS No. 2 362 494, the contents of the vessel may be expanded in a stirred container, preferably kept at normal pressure and the distillable components are removed from the mixture by heating. The contents of the vessel are then generally hydrolyzed.

The hydrolysis itself may be carried out in a down-pipe, as described in DE-PS No. 2 362 494. The disadvantage is that, in view of the short contact times, hydrolysis is often incomplete and large quantities of water are consumed.

U.S. Pat. No. 4,221,691 describes a hydrolysis process in which the unpleasant property that the hydrolyzates have of sticking is prevented by the addition of mineral oil. However, since the hydrolyzates are regarded as worthless and are dumped, the additional organic pollution they cause is a disadvantage.

It is known from U.S. Pat. No. 4,408,030 that the problem of sticking can also be overcome by maintaining a minimum chlorine content, although technically this is difficult to do.

In all the processes mentioned above, a hydrochloric acid suspension is formed in which the more or less solid hydrolyzate is regarded as worthless and has to be dumped. However, the hydrolyzates are not without problems because they generally contain 2 to 10% predominantly metallic copper which can be partly eluted from the dumped hydrolyzate, thus endangering the ground water. In addition, most of the hydrolyzates obtained are vulnerable to oxidation and, in some cases, even show a tendency to ignite spontaneously so that they cannot be safely dumped.

Now, U.S. Pat. No. 4,758,352 describes a process in which the hydrolysis is carried out in water or a heavily diluted hydrochloric acid in a stirred container which is equipped with a high-speed disk stirrer, but not with baffles so that a vortex into which the material to be hydrolyzed is introduced can form. The preferred temperature is between 60° and 90° C. A suspension of finely divided solid hydrolyzates, in which more than 90% of the solid particles are smaller than 5 mm in diameter, is thus obtained.

The suspensions thus obtained are then oxidized with oxygen-containing gases which, according to the invention cited above, is preferably done with technically pure oxygen under a pressure above atmospheric pressure.

On completion of oxidation, solids and copper-containing liquid are separated from one another.

The process according to U.S. Pat. No. 4,758,352 gives a disposable, compact, non-gasing solid with no elutable heavy metals which is thermally inert in the context of the invention and may thus be safely dumped.

SUMMARY OF THE INVENTION

Now, the present invention relates to a process for working up high-boiling, solids-containing residues obtained in the synthesis of organoclorosilanes which are hydrolyzed and then oxidized, characterized in that a surface-active agent which hydrophilicizes the surface of the solids is added during hydrolysis and/or oxidation.

The addition of a surface-active agent in accordance with the invention is not confined to the combination of hydrolysis and oxidation and may also be applied where hydrolysis is carried out without subsequent oxidation. In general, the better wetting reduces the tendency of the hydrolyzate to stick, thus reducing contamination of the product-carrying parts of the plant.

Hydrolysis preferably comprises adding the surface-active agent to the water or the heavily diluted hydrochloric acid, which is fed to the stirred container comprising a high-speed disk stirrer for hydrolyzing the high-boiling solids-containing residue from the synthesis of organochlorosilanes, and thus hydrophilicizing the surface.

Oxidation preferably comprises adding the surface-active agent hydrophilicizing the surface to the suspension to be oxidized during filling of the oxidation reactor. It is also possible to add part of the surface-active agent during hydrolysis and another part during oxidation.

The surprising advantage of the working-up process according to the invention is that it provides for better wetting of the high-boiling, solids-containing residue to be hydrolyzed and hence for more effective hydrolysis and that oxidation, which according to the invention is preferably carried out by exposing the suspension obtained during hydrolysis to technically pure oxygen under a pressure above atmospheric pressure at temperatures of 80°±10° C., is not accompanied by any flotation and foaming effects, which could adversely affect the conduct of the reaction.

The type of substances which influence the surface can be very different. They are generally recruited from the class of surfactants and are therefore mainly organic in character. In the present cases, alkyl and alkylbenzene sulfonates have proved to be particularly suitable, although the invention is not confined to the use of surface-active agents from this group. On the contrary, it is possible to use any surface-active agents, which effectively wet the hydrolyzate and which are sufficiently stable in the hydrochloric acid medium, or mixtures thereof.

Alkyl sulfonates which may be successfully used are known, for example, under the trade names of "Mersolat H" and "Mersolat W" (Bayer AG). Alkylbenzene sulfonates, which are equally effective, are known, for example, under the trade name of "Marlon A 357" (Chemische Werke Hüls).

Mixtures are also understood to include formulations of the type used, for example, as foam inhibitors for surfactant-containing solutions. The foam inhibitor DNE (Bayer AG), a mixture of fatty acid esters and higher hydrocarbons with carboxylic acid salts, may be successfully used in accordance with the invention. In this case, the surface-active agents are not from the class of alkyl and alkylbenzene sulfonates.

The expert knows that a number of compounds and formulations of different compounds may be used and that success generally requires close adaptation to the particular medium to be wetted. It is important that the surface is rendered hydrophilic and that the addition does not itself lead to problems such as foaming for example.

The quantity of surface-active agent required depends on the quantity of solids present in the suspension and their fineness.

In most cases, suspensions of 20 to 30% by weight solid hydrolyzate, determined as moist filter cake, are required for hydrolysis. Experience has shown that between 100 and 10,000 ppm, expressed as parts by weight of the active substance based on the suspension as a whole, have to be used for suspensions such as these. Additions of 200 to 5000 ppm active substance, based on the suspension as a whole, are preferred.

BRIEF DESCRIPTION OF THE DRAWING

The preferred embodiment of the process according to the invention is described in detail in the following with reference to the accompanying drawing and the Examples which are purely illustrative and are not intended to limit the invention in any way.

DETAILED DESCRIPTION OF THE INVENTION

Figure 1:
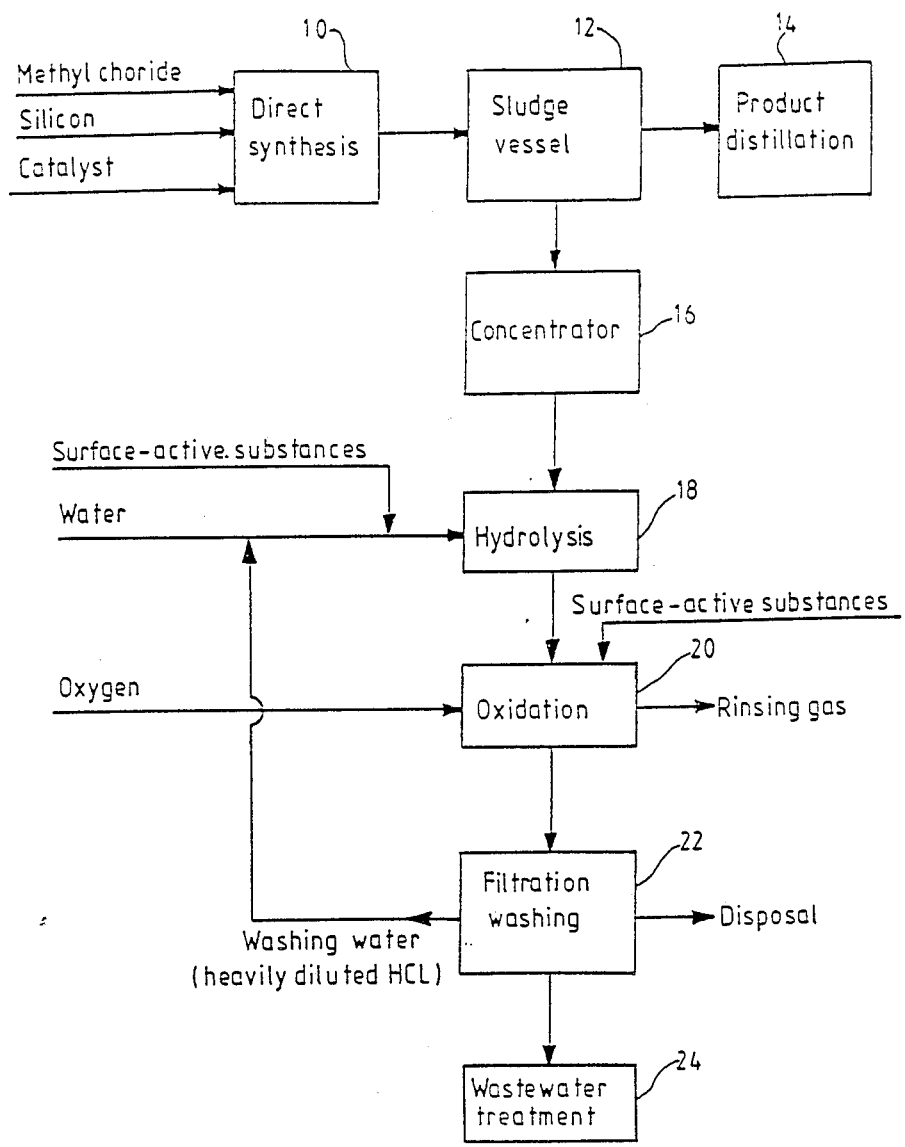
FIG. 1 schematically depicts the invention process.

FIG. 1 shows the standard procedure. Gaseous reaction products, unreacted methyl chloride and fines enter the slude vessel 12 from the "direct synthesis reactors" 10. The non-volatile constituents are collected in the sludge vessel 12. The volatile constituents leave the vessel 12 for the product distillation stage 14. By means of a cycle valve, the non-volatile contents are expanded and introduced into a concentrator 16 to recover compounds which are volatile at atmospheric pressure.

Hydrolysis is carried out with water or dilute HCl in a stirrer-equipped reaction vessel 19.

Now, surface-active substances may be added in accordance with the invention to the water required for hydrolysis through the water inlet or, if desired, not until the next step, i.e., during filling of the oxidation reactor 20, in which the liquid is exposed to the gas containing the elemental oxygen; partial quantities may optionally be added at both places. After oxidation, the solid is separated from the aqueous liquid in a suitable filtration unit 22, the aqueous liquid is fed to a suitable wastewater treatment plant 24 and the solid is washed and then dumped. The washing water may optionally be reused for hydrolysis.

The invention will now be described with reference to the following non-limiting examples.

EXAMPLE 1

Example 1 demonstrates the effect which the addition of detergent constituents from the group of alkyl and alkylbenzene sulfonates has on the foaming of a hydrolyzed suspension gassed with air.

3 kg of a hydrolysis suspension containing 20% by weight moist solids, which had come from industrial direct synthesis, were gassed in a gassing apparatus with three baffles and a gassing stirrer (gassing stirrer diameter 4.6 cm, stirring speed 1585±30 r.p.m., vessel diameter=15 cm, vessel height=60 cm, filling level approx. 17.5 cm). In another test under the above-mentioned conditions, 2 g of a 30% solution of Mersolat ® (Bayer AG) were added to the suspension before gassing. 4 g Marlon A 375 ® (Chemische Werke Marl Hüls) were added to a third suspension. The behavior is shown in Table 1.

TABLE 1

| Quantity added: 3 ml | Foam height during gassing | Settling behavior of solids after gassing |
|---|---|---|
| Comparison test with no addition | 11 cm | approx. 50% of the solids float |
| 2 g "Mersolat H" (30%) | 1 cm | more than 90% of the solids sediment |
| 4 g "Marlon A 375" (30%) | 1 cm | more than 90% of the solids sediment |

"Mersolat H": sodium alkyl sulfonate
"Marlon A 375": sodium alkylbenzene sulfonate

EXAMPLE 2

In the apparatus described in Example 1, quantities of 5000 ppm (based on suspension) of the organic foam inhibitors DNE on OC 6003 were added to a suspension, which forms an 18 cm tall layer of foam under gassing conditions without the addition of a surface-active agent.

Where the foam inhibitor DNE was added, the foam height was reduced to 3 cm. Where the foam inhibitor OC 6003 was added, the foam height was again reduced to 3 cm.

Whereas, after the termination of gassing in the untreated suspension, approximately 80% of the solids floated on the surface, approximately 50% of the solids sedimented where DNE was added and approximately 100% where OC 6003 was added.

Foam inhibitor DNE (Bayer AG):

A mixture of fatty acid esters and higher hydrocarbons with carboxylic acid salts.

Foam inhibitor VPOC 6003 (Bayer AG):

Alkyl polypropylene polyethylene glycol ether.

It will be appreciated that the instant specification and claims are set forth by way of illustration and not limitation, and that various modifications and changes may be made without departing from the spirit and scope of the present invention.

What is claimed is:

1. A process for the hydrolysis and oxidation of high-boiling, solids-containing residues obtained in the synthesis of organochlorosilanes which are hydrolyzed and then oxidized with a gas comprising oxygen, comprising adding during hydrolysis and/or oxidation a surface-active agent which hydrophilicizes the surface of the solids.

2. A process as claimed in claim 1, wherein the surface-active agent is a detergent constituent.

3. A process as claimed in claim 1, wherein the surface-active agent is an alkyl sulfonate or an alkylbenzene sulfonate.

4. A process according to claim 1, wherein the surface-active agent is a mixture of fatty acid esters and higher hydrocarbons with carboxylic acid salts.

5. A process as claimed in claim 1, wherein the surface-active agent is in an amount of from 100 ppm to 10,000 ppm, based on a suspension of hydrolyzed solids-containing residues.

6. A process as claimed in claim 5, wherein the amount is 200 to 5,000 ppm.

* * * * *